United States Patent [19]

Kuzma

[11] Patent Number: 4,898,183
[45] Date of Patent: Feb. 6, 1990

[54] APPARATUS AND METHOD FOR INSERTION OF COCHLEAR ELECTRODE ASSEMBLY

[75] Inventor: Janusz Kuzma, Cherrybrook, Australia

[73] Assignee: Cochlear Pty. Limited, Lane Cove, Australia

[21] Appl. No.: 368,979

[22] Filed: Jun. 20, 1989

Related U.S. Application Data

[63] Continuation of Ser. No. 77,445, Jul. 24, 1987, abandoned.

[51] Int. Cl.$^4$ .............................................. A61N 1/00
[52] U.S. Cl. ................................... 128/784; 128/420.6
[58] Field of Search ...................... 128/420.6, 789, 639, 128/642, 784, 419 P, 785

[56] References Cited

U.S. PATENT DOCUMENTS

| | | | |
|---|---|---|---|
| 4,284,085 | 8/1981 | Hanseu et al. | 128/420.6 |
| 4,514,589 | 4/1985 | Aldinger et al. | 128/419 P |
| 4,522,209 | 7/1985 | Patrick et al. | 128/420.6 |
| 4,706,682 | 11/1987 | Stypulkowski et al. | 128/789 |

FOREIGN PATENT DOCUMENTS

| | | | |
|---|---|---|---|
| 4160078 | 6/1979 | Australia | 128/420.6 |
| 4656379 | 11/1979 | Australia | 128/420.6 |
| 0085417 | 8/1983 | European Pat. Off. | 128/420.6 |
| 0109304 | 5/1984 | European Pat. Off. | 128/420.6 |
| 80/02231 | 10/1980 | PCT Int'l Appl. | 128/419 P |
| 2057272 | 4/1981 | United Kingdom | 128/420.6 |

Primary Examiner—Francis Jaworski
Assistant Examiner—George Manuel
Attorney, Agent, or Firm—Gottlieb, Rackman & Reisman

[57] ABSTRACT

An apparatus and method for insertion of a cochlear implant. The method includes sliding a collar on to the rear end of a cochlear electrode lead, applying glue to the forward end of the collar, and putting a gripping tool configured for squeeze-fit placement in the free rear end of the collar.

13 Claims, 4 Drawing Sheets

APPARATUS AND METHOD FOR INSERTION OF COCHLEAR ELECTRODE ASSEMBLY

This application is a continuation of Application Ser. No. 077,445; filed July 24, 1987, now abandoned.

DESCRIPTION

This invention relates to an insertion tool for a cochlear implant, and a method for using that tool to insert a cochlear electrode lead into a patient's ear.

The stimulating electrode assembly of a cochlear implant is placed inside the cochlear partition, commonly into the scala tympani. A major problem with conventional electrode leads is in inserting them into the cochlea without irreversibly damaging the auditory nerve fibers, and the electrodes and lead wires of the electrode lead. In the prior art, electrode leads are surgically inserted along the line of sight through the round window and along the basal turn of the cochlea, either with an alligator forceps or with Y-shaped claws. The alligator forceps adequately control the force and direction of the electrode insertion, but risk of damage to the electrodes is high. The forceps also must be periodically removed and replaced to correctly orient the electrode array in the cochlea, since it can grip the electrode lead only through a limited angle of rotation. The Y-shaped claws minimize damage to the electrode, but it cannot be used to apply insertion force in the optimum direction, along the line of sight. Since it cannot grip the electrode lead, it also cannot be used to rotate the electrode to correctly place it in the cochlea.

An object of my invention is to provide an insertion tool and a technique for insertion of the electrode lead which both protects the electrode assembly and allows successful manipulation of the electrode lead into the cochlea.

In accordance with the principles of my invention, the electrode lead is provided with a collar, preferably made of silicone rubber. The collar is affixed to the rear of the electrode lead at a predetermined point above the electrode assembly. The collar is expanded in Freon or other suitable gas, so that the inner diameter of the collar is slightly greater than the outer diameter of the electrode lead. This enables the collar to slip over the lead during manufacture. After placement of the collar, the Freon evaporates, and the collar returns to its original dimensions (equivalent to the outer diameter of the lead). This shrinking results in a snug friction fit. Glue (preferably silastic A) is applied to the forward edges of the collar. The collar is positioned so that it is located outside the round window after insertion is completed.

The insertion or gripping tool has a rounded end, configured like a thumbnail at the tip, designed to fit between the collar and the lead. A major advantage of my invention is that the squeeze or friction fit of the gripping tool to the electode lead (through the collar) completely prohibits possible damage to the electrode array as may occur with use of alligator forcepts. This mode of attachment also permits optimum application of the insertion force directly along the axis. Further, the surgeon can use the gripping tool to rotate the electrode lead without fear that the tool will slip off the lead and damage the electrode assembly or the delicate tissues of the patient's ear. This contrasts with the prior art Y-shaped claws which cannot be used to apply force along the line of sight or to grip and rotate the electrode lead. Although the prior art alligator forceps adequately control the force and direction of the electrode insertion, it must be periodically removed from the lead and replaced at a point further back on the lead in order to completely insert the electrode lead into the cochlea. With my invention, the surgeon may apply constant forward force along the axis without removing the gripping tool at all.

My invention can also be used with both symmetric and non-symmetric electrodes. With non-symmetric electrodes, the gripping tool is placed under the collar so that it is directly above the active electrodes (e.g. 180 degrees away). A mark is placed on the front of the handle of the gripping tool so that when the surgeon inserts the electrode lead into the cochlea and the electrode assembly is no longer visible, the surgeon is able to determine the orientation of the active electrodes and to rotate the electrode lead to correctly place the active electrode assembly in the cochlea. With symmetric electrodes, the placement of the tool with respect to the array is not important.

After insertion of the electrode array is completed, the gripping tool is removed by sliding it along the axis of the lead; the lead can be held steady (so that removal of the tool does not remove the lead) by temporary placement of the Y-shaped claws on the collar.

Further objects, features, and advantges of my invention will become apparent upon consideration of the following detailed description in conjunction with the drawings, in which.

Figure 3A:
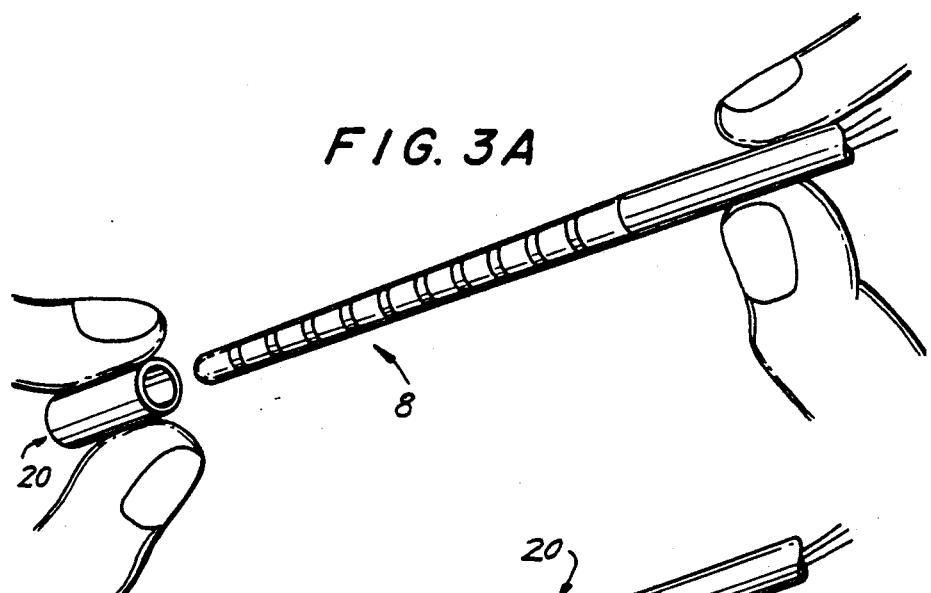
Figure 3B:
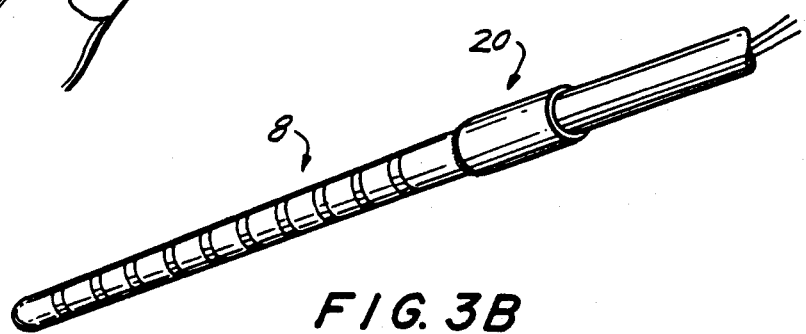
Figure 3C:
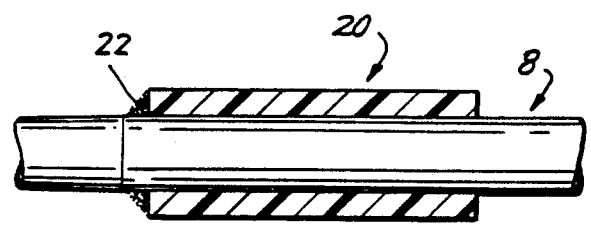
Figure 4A:
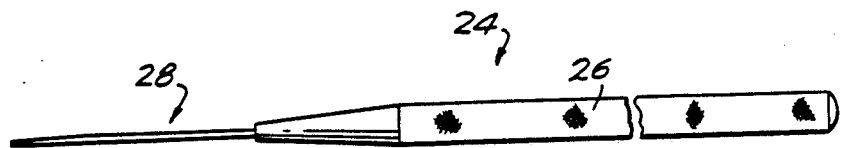
Figure 4B:
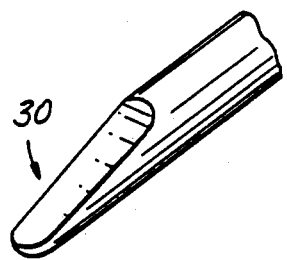
Figure 5A:
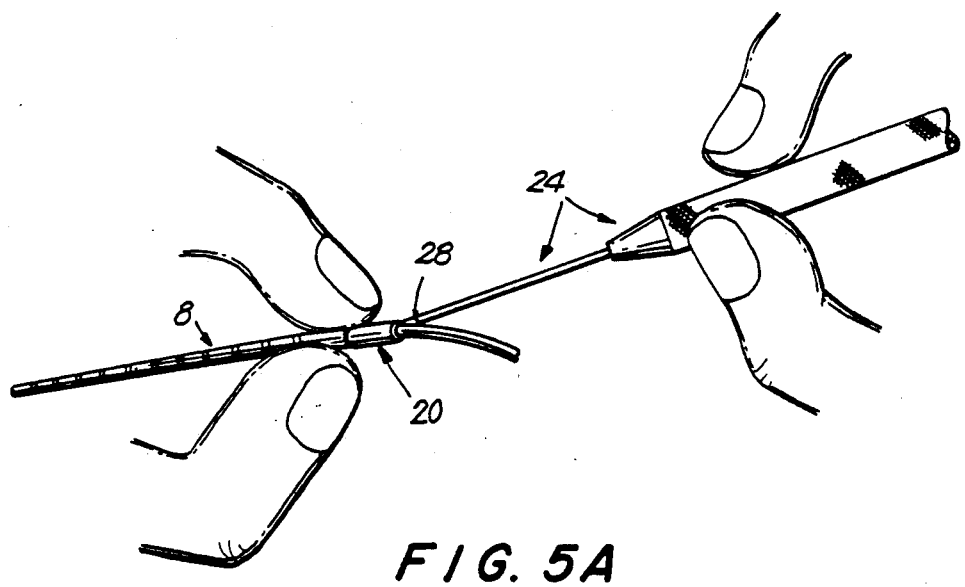
Figure 5B:
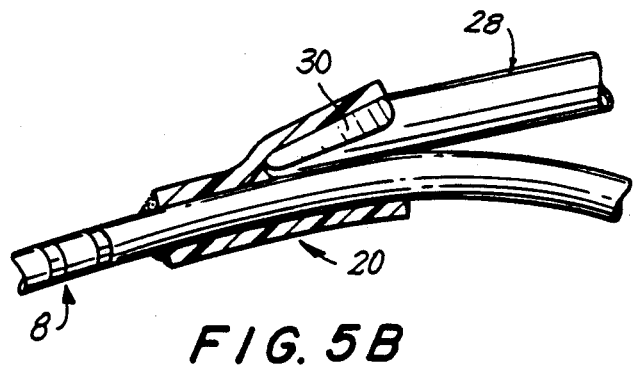
Figure 5C:
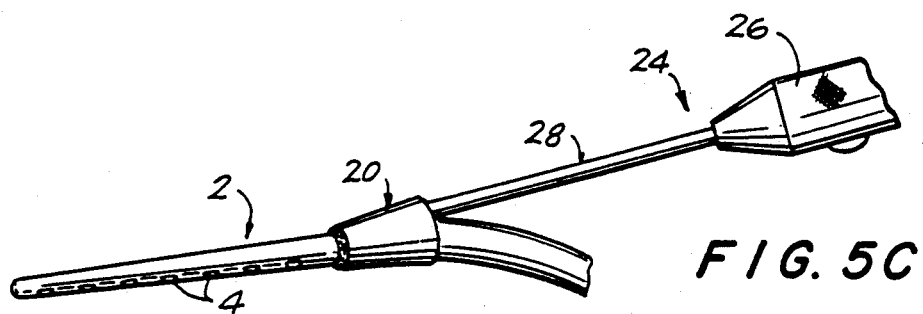

FIG. 3A-C illustrate the preferred method of placing the collar around the elecotde lead during manufacture;

FIG. 4A is an illustration of the gripping tool;

FIG. 4B is an enlarged view of the tip of the gripping tool;

FIGS. 5A-C illustrate the preferred method of using the insertion tool with the electrode lead.

Figure 1A:
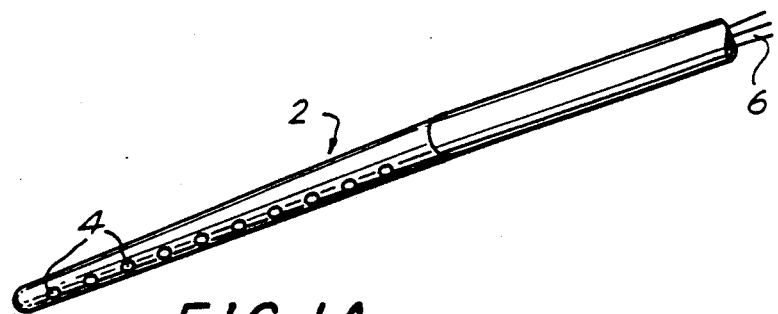
FIG. 1A is an illustration of a prior art non-symmetric electrode lead.
Figure 1B:
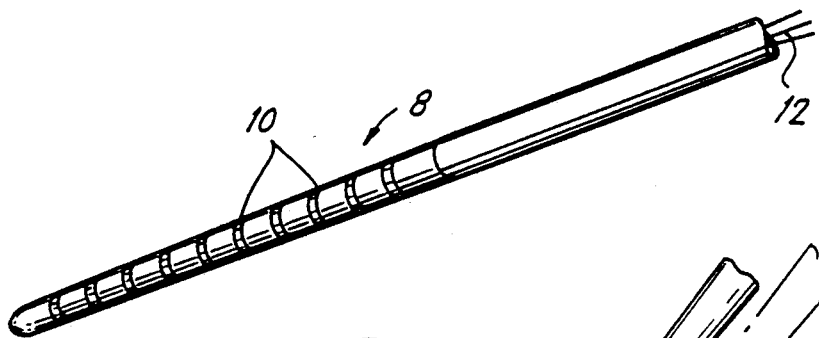
FIG. 1B is an illustration of a prior art symmetric electrode lead.
Figure 2:
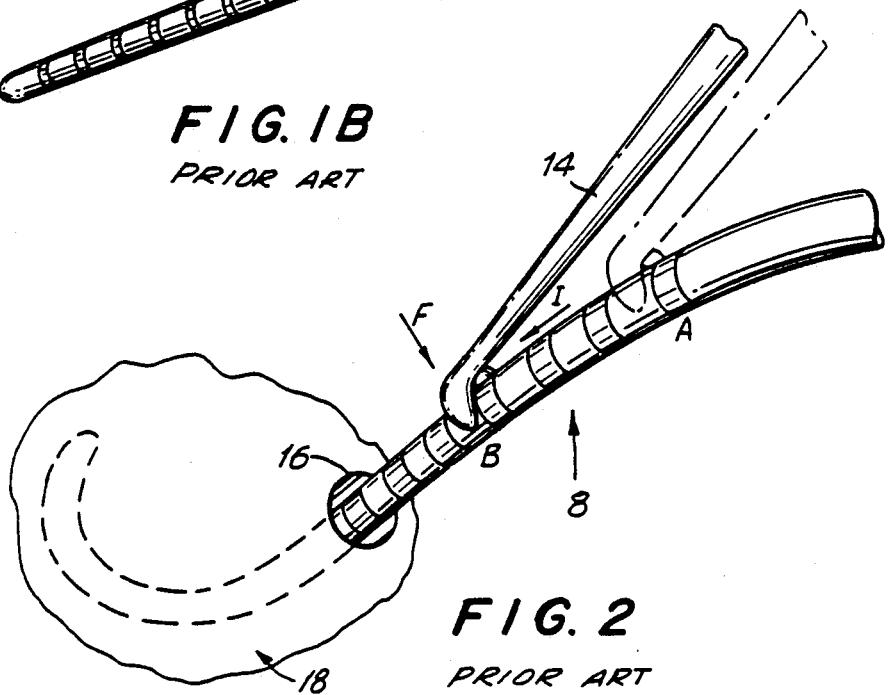
FIG. 2 illustrates the prior art method of inserting the electrode lead into the cochlea.

FIG. 1A is an illustration of a prior art non-symmetric or localized electrode lead 2, with active electrodes 4 and electrode lead wires 6. FIG. 1B shows a prior art symmetric or banded electrode lead 8, with active electrodes 10 and electrode lead wires 12. The prior art method of inserting an electrode lead into the cochlea is shown in FIG. 2. To achieve insertion, force must be applied along the axis of electrode lead 8 (direction I). When prior art Y-shaped claws 14 are used, this force is generated from friction between the claws and the lead. Since the lead is smooth and slippery, a large force F, normal to the axis, is required, which may result in bending or undesirable rotation of the lead. Further, in order to push lead 8 through round window 16 and along basal turn 18 of the cochlea, the surgeon must periodically remove and replace claws 14 (from position B to A in FIG. 2).

In the preferred embodiment of my invention, a collar is placed on the electrode lead to the rear of the electrode assembly. In FIGS. 3A-3C, the preferred method of placing collar 20 around electrode lead 8 is illustrated. In FIG. 3A, a 5-6 mm length collar 20, made of silastic tubing, silicone rubber or other suitable material, is slipped over the front end of lead 8 to rest at a point approximately 26 mm behind the last electrode. Collar 20 is expanded in Freon to produce an inner diameter of 0.6 mm, which is slightly larger than the outer diameter of electrode lead 8, so as to facilitate placement of collar 20 over lead 8 and to allow for a snug friction fit after evaporation of the Freon. Collar 20 has a wall thickness of 0.2-0.3 mm. FIG. 3B shows the placement of collar 20 on lead 8. In FIG. 3C, an enlarged view of collar 20 and lead 8, glue 22 (preferably silastic A) is applied to the front edges of collar 20, permanently affixing collar 20 to lead 8.

FIGS. 4A and 4B show gripping tool 24 which is adapted for use with collar 20. FIG. 4A is an illustration of gripping tool 24, with a 110 mm length handle 26 and a 40 mm tip 28. FIG. 4B is an enlarged view of the front of tip 28, with all sharp edges removed to form a rounded end 30, with a length of 3-3.5 mm. In FIG. 5A, rounded end 30 is placed gently under the rear end of collar 20, allowing the tip of the insertion tool to be attached to lead 8, removed from the vicinity of the electrodes themselves. FIG. 5B is an enlarged view of the location of rounded groove 30 under collar 20.

This technique of attachment permits the surgeon to apply force directly along the axis, in the optimum direction along the line of sight through the round window. Possible damage to the electrode lead is minimized, and the surgeon does not need to periodically remove and replace the gripping tool to push the lead forward. The friction fit of the gripping tool to the lead also permits the surgeon to rotate the lead and corectly orient it in the cochlea without fear that the tool may slip off the lead. When the tool is used to insert non-symmetric or localized electrode lead 2 in FIG. 5C, the gripping tool is placed 180 degrees from active electrodes 4, and a mark is placed on the front of handle 26, indicating the direction of the active electrodes. This enables the surgeon to determine the location of active electrodes 4 when the lead has been inserted through the round window and the active electrodes are no longer visible, permitting the surgeon to correctly orient the active electrodes with respect to the cochlear nerves.

After insertion of the electrode assembly is completed, the collar is located outside the round window. Removal of the gripping tool from the collar is accomplished by sliding the tool along the axis of the lead; the lead can be held steady (so that removal of the tool does not remove the electrode assembly from the cochlea) by the temporary placement of prior art Y-shaped claws on the collar.

Although the invention has been described with reference to a particular embodiment it is to be understood that this embodiment is merely illustrative of the application of the principles of the invention. Numerous modifications may be made therein and other arrangements may be devised without departing from the spirit and scope of the invention.

I claim:

1. A cochlear electrode lead assembly comprising a lead with a distal end and a proximal end including an array of electrodes on an external surface of said lead proximate said distal at one end and a resilient collar surrounding said lead and attached thereto at a region between said array and said proximal end, and means for permanently affixing a first circumferencial end of said collar to said lead only at said region.

2. A cochlear electrode lead assembly in accordance with claim 1, wherein said resilient collar has an inner diameter substantially equivalent to an outer diameter of said lead so as to frictionally engage said lead, said collar being sufficiently resilient to stretch so as to receive a member between said collar and said lead.

3. A cochlear electrode lead assembly in accordance with claim 2, wherein said member is a tip of an insertion tool for inserting said lead into the ear.

4. A cochlear electrode lead assembly in accordance with claim 3, wherein said insertion tool is comprised of a handle for said tip and said tip has rounded edges for insertion between said collar and said lead at an end of said collar remote from said assembly.

5. The cochlear electrode lead assembly of claim 3, wherein a second circumferential end of said collar surrounds said lead without being attached thereto so that a member may be received between said lead and said collar.

6. A cochlear electode lead assembly in accordance with claim 1, wherein said collar is comprised of silicone rubber.

7. A cochlear electrode lead assembly in accordance with claim 1, wherein said means for affixing is cured silastic A affixed to said circumferencial end of said collar and said lead.

8. A method of making an insertion mechanism for a cochlear implant lead having an electrode assembly, comprising the steps of:
   (a) expanding a resilient collar so that an inner diameter of said collar is greater than an outer diameter of said lead,
   (b) sliding said expanded collar on to said lead to rest at a point beyond said electrode assembly,
   (c) permitting said collar to return to said inner diameter equivalent to said outer diameter of said lead, and
   (d) permanently affixing said collar to said lead by applying adhesive only to a circumferencial end of said collar adjacent to said electrode assembly.

9. The method of making an inssertion mechanism in accordance with claim 8, wherein said collar is formed of silicone rubber.

10. A method of making an insertion mechanism in accordance with claim 8, wherein in step a said collar is exposed to a material which causes said collar to temporarily expand.

11. A method of making an insertion mechanism in accordance with claim 8, wherein said material is Freon.

12. A method of making an insertion mechanism in accordance with claim 8, wherein in step c said material is permitted to evaporate from said collar.

13. A cochlear electrode electrode assembly comprising:
   a lead for insertion into the cochlear, said lead having, at one end thereof, an array of elecctrodes on an external surface of said lead;
   a resilient collar surrounding said lead along a portion of its length adjacent said one end and attached to said lead at an end of said collar adjacent said array, said collar being sufficiently resilient to stretch so as to receive a member between said collar and said lead;
   an insertion tool for inserting the end of said lead having said array into the cochlear, said tool having a tip sized and shaped for substantially parallel placement between said lead and said collar.

* * * * *

UNITED STATES PATENT AND TRADEMARK OFFICE
CERTIFICATE OF CORRECTION

PATENT NO. : 4,898,183
DATED : February 6, 1990
INVENTOR(S) : Janusz Kuzma

It is certified that error appears in the above-identified patent and that said Letters Patent is hereby corrected as shown below:

Claim 1 is corrected to read as follows:
1. A cochlear electrode lead assembly comprising a lead with a distal end and a proximal end including an array of electrodes on an external surface of said lead proximate said distal end and a resilient collar surrounding said lead and attached thereto at a region between said array and said proximal end, and means for permanently affixing a first circumferencial end of said collar to said lead only at said region.

Signed and Sealed this

Seventh Day of May, 1991

*Attest:*

HARRY F. MANBECK, JR.

*Attesting Officer*      *Commissioner of Patents and Trademarks*